United States Patent [19]
Margulies

[11] Patent Number: 5,700,292
[45] Date of Patent: Dec. 23, 1997

[54] SPINAL STABILIZATION SYSTEM AND METHOD

[75] Inventor: Joseph Y. Margulies, Pleasantville, N.Y.

[73] Assignee: Hospital for Joint Diseases, New York, N.Y.

[21] Appl. No.: 528,801

[22] Filed: Sep. 15, 1995

Related U.S. Application Data

[63] Continuation of Ser. No. 273,371, Jul. 11, 1994, abandoned, which is a continuation of Ser. No. 973,294, Nov. 9, 1992, abandoned.

[51] Int. Cl.⁶ ................................................. A61F 2/10
[52] U.S. Cl. ................................. 623/17; 606/61
[58] Field of Search ...................... 606/60, 61, 62, 606/64, 53, 54, 57, 71, 73; 623/16, 17

[56] References Cited

U.S. PATENT DOCUMENTS

| | | |
|---|---|---|
| 3,848,601 | 11/1974 | Ma et al. |
| 4,047,524 | 9/1977 | Hall. |
| 4,349,921 | 9/1982 | Kuntz. |
| 4,456,005 | 6/1984 | Lichty .................... 128/92 A |
| 4,479,491 | 10/1984 | Martin. |
| 4,554,914 | 11/1985 | Kapp et al. ................. 606/61 |
| 4,573,454 | 3/1986 | Hoffman. |
| 4,599,086 | 7/1986 | Doty. |
| 4,858,601 | 8/1989 | Glisson ..................... 606/104 |
| 4,878,915 | 11/1989 | Brantigan. |
| 4,913,134 | 4/1990 | Lugue ...................... 606/61 |
| 4,936,848 | 6/1990 | Bagby. |
| 5,007,909 | 4/1991 | Rogozinski. |
| 5,015,247 | 5/1991 | Michelson. |
| 5,055,104 | 10/1991 | Ray. |
| 5,062,850 | 11/1991 | MacMillian et al. |
| 5,127,912 | 7/1992 | Ray et al. ................... 606/61 |

FOREIGN PATENT DOCUMENTS

| | | | |
|---|---|---|---|
| 0644473 | 1/1979 | U.S.S.R. | .............. 606/61 |
| 0770482 | 10/1980 | U.S.S.R. | .............. 606/57 |
| 1540812 | 2/1990 | U.S.S.R. | .............. 606/57 |
| 1598991 | 10/1990 | U.S.S.R. | .............. 606/57 |

*Primary Examiner*—Debra S. Brittingham
*Attorney, Agent, or Firm*—Stephen E. Feldman

[57] ABSTRACT

A spinal stabilization system for fixing vertebrae and sacrum having anterior and posterior aspects. The system comprises a plurality of rods or plates disposed over the vertebrae and/or sacrum, at least one rod or plate disposed anteriorly and at least one disposed posteriorly, and a plurality of bolts and nuts extending laterally through said vertebrae and/or sacrum and attached to the rods.

A method for installing a spinal stabilization system to fix vertebrae and/or sacrum, comprising the steps of: exposing the spine anteriorly and posteriorly to reveal a level of vertebrae and/or sacrum; inserting a pair of beam means through the vertebrae and/or sacrum; repeating the exposing and inserting steps for a next level of vertebrae and/or sacrum; disposing column means over the anterior and posterior aspects of the two levels of vertebrae and/or sacrum; and connecting the ends of the beam means at each vertebrae and/or sacrum level to the column means.

17 Claims, 3 Drawing Sheets

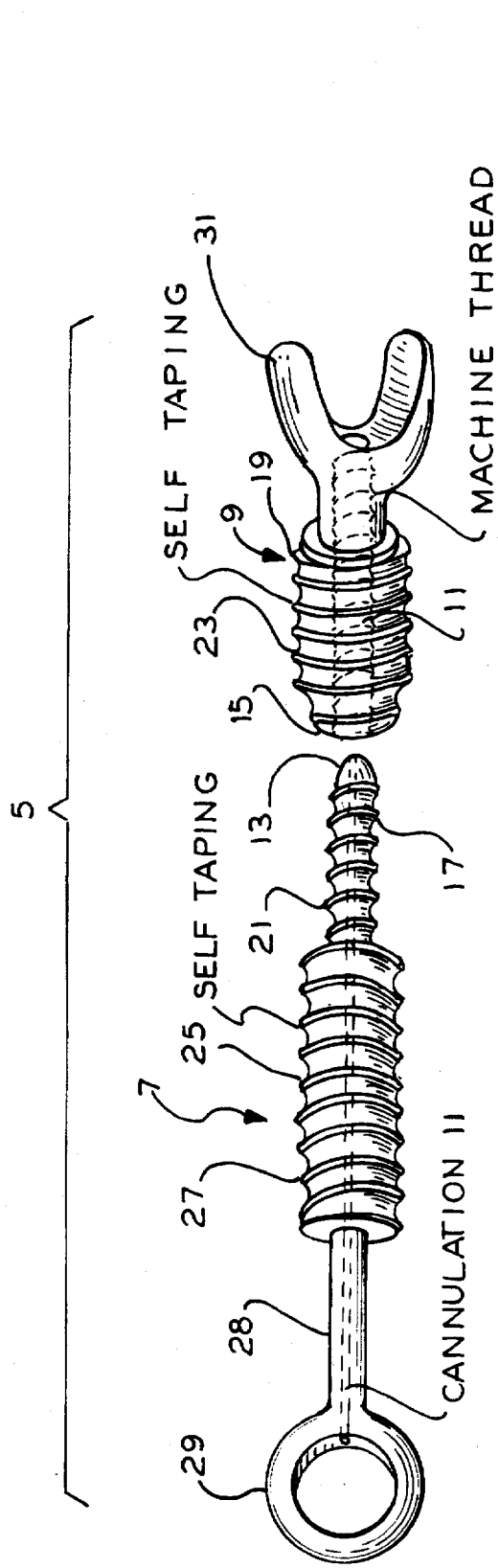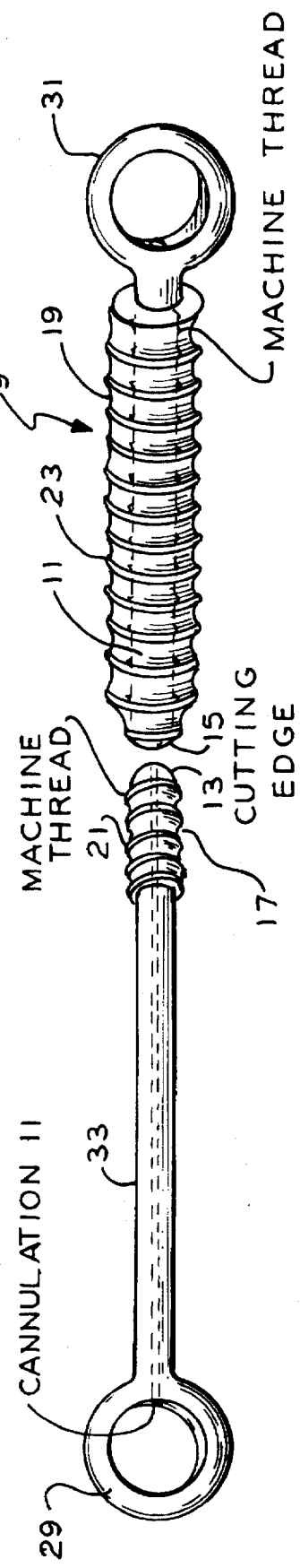

SPINAL STABILIZATION SYSTEM AND METHOD

This application is a continuation of application Ser. No. 08/273,371, filed Jul. 11, 1994, now abandoned, which is a con. of Ser. No. 07/973,294 filed Nov. 9, 1992, now abandoned.

FIELD OF THE INVENTION

This invention relates to a spinal stabilization system and method for fixing vertebrae and sacrum.

BACKGROUND OF THE INVENTION

Spinal stabilization with instrumentation or system is a common method to treat many pathological process in the spine. Stabilization means eliminating the movement between spinal units, and to restore the spinal function to a certain extent. Stabilization is performed by fusing spinal elements to each other. The technical objective of the stabilization is to achieve a solid bony fusion. This is usually done by creating a "fracture situation" between adjacent vertebrae, fixating them mechanically by metal implants and letting the natural bone healing process to occur, creating a fusion mass, which becomes one piece of bone. The task of the instrumentation implanted in the spine is to hold the fractured or injured bone surfaces next to each other until healing/fusion occur.

The stability of a construct is not sufficient in the long term, without bone fusion. The surgical state of the art is a circumferential (anterior and posterior) approach, to rebuild the anterior column and the posterior column(s) separately. Each of the constructs, anterior or posterior, has characteristics and mechanical qualities, based on its design, biomechanics and surgical placement.

The disadvantages of the circumferential approach are several: too much metal in two different sets of devices; the construct may fail to promote stress sharing and may create stress shielding; and the construct might be too strong for osteogenic bone, and cut through it.

The major problem is what to do with bone tissue which is of poor quality, or with spines in which adequate attachment of the construct to the bone is not achievable.

SUMMARY OF THE INVENTION

The present invention in its broadest aspect provides a spinal stabilization system for fixing vertebrae and/or sacrum of the spinal or vertebral column, having anterior and posterior aspects. The system comprises a plurality of substantially rigid, elongated column means disposed over the vertebrae and/or sacrum. At least one of the column means is disposed over the anterior aspects of the vertebrae and/or sacrum and at least another of the column means is disposed over the posterior aspect of the vertebrae and/or sacrum. A plurality of substantially rigid, elongated beam means which extend through these vertebrae and/or sacrum are attached to the column means.

Additionally, the present invention in its broadest aspect provides a method of installing a spinal stabilization system to fix vertebrae and/or sacrum. The steps comprise exposing the spine anteriorly and posteriorly to reveal a level of vertebra and/or sacrum, inserting a one or pair of beam means through the vertebrae and/or sacrum, repeating the exposing and inserting steps for a next level of vertebra and/or sacrum, disposing column means over the anterior and posterior aspects of the two levels of vertebra and/or sacrum, and connecting the ends of the beam means at each vertebra and/or sacrum level to said column means.

The principal object of the invention is to provide a construct incorporating a new concept that combines the anterior and posterior constructs into a single unitary construct.

Another object of the invention is to provide an improved construct or cage and method in which bone and bone graft can heal to a solid fusion.

A further object of the invention is to provide an improved solid construct, yet having increased stress sharing.

BRIEF DESCRIPTION OF THE DRAWINGS

FIG. 4A is a perspective view of a preferred embodiment of a single unassembled bolt and nut portions of the present invention;

FIG. 4B is a perspective view of a preferred embodiment of another single unassembled bolt and nut portions of the present invention for use with smaller vertebrae.

DESCRIPTION OF THE PREFERRED EMBODIMENT

Figure 3:
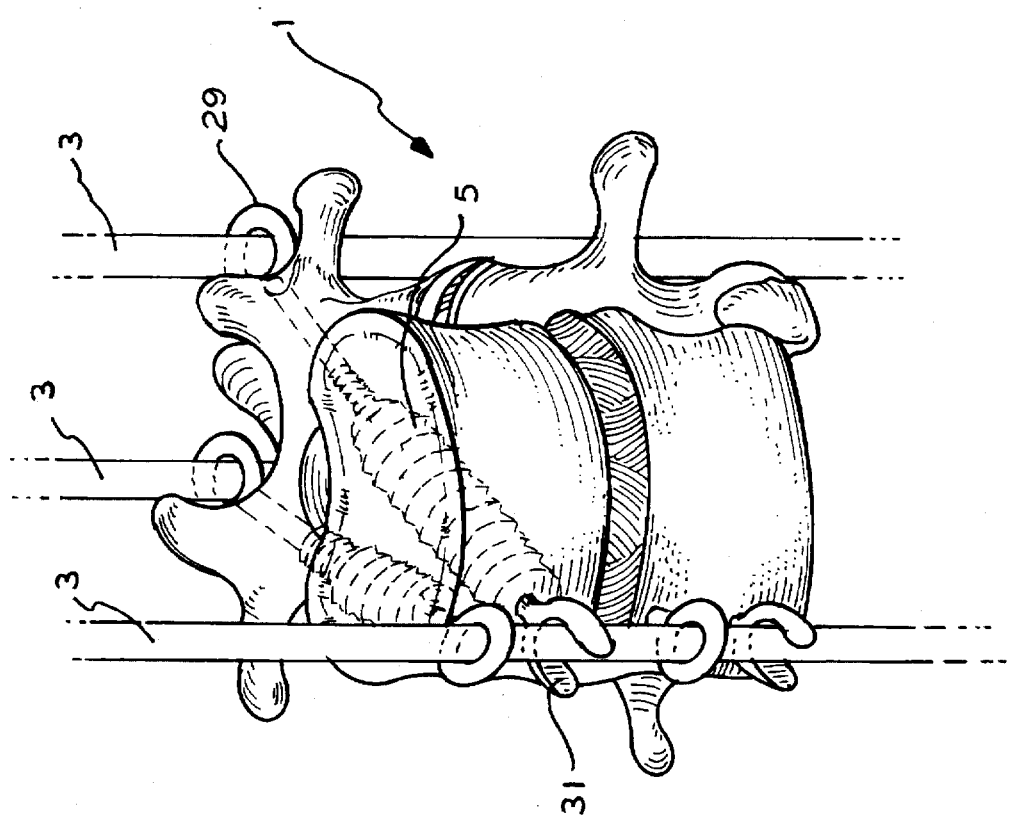
FIG. 3 is a perspective view of the implanted spinal stabilization system of the present invention.

The preferred embodiment of the spinal stabilization or fixation system for fixing vertebrae and/or sacrum having anterior and posterior aspects is generally designated by the reference character 1 and its complete assembly is shown in FIG. 3. The system comprises conventional, column means 3, three in number, each of which is a rigid elongated rod or plate, one of which disposed over the anterior aspect of at least two such vertebrae and/or sacrum bones or bodies, and as shown in this figure vertebrae, and two of which rods are disposed over the posterior aspects of the two vertebrae. These rods 3 are attached to beam means 5, four in number, each of which is a rigid elongated beam means which extend through individual vertebrae. It should be noted however that two or three or more rods could be used. Referring specifically to FIG. 4A, which illustrates in detail a single beam means 5 which comprise a pedicle bolt section 7 and a nut section 9, each of which sections are adapted to join each other when they are inserted through a vertebra when the system 1 is installed. Each of these bolt and nut sections 7 and 9, respectively, preferably have an aperture or cannulation 11 extending along the longitudinal axes thereof; such cannulation 11 is however optional. Each of the bolt and nut sections 7 and 9, respectively, have a cutting end portion 13 and 15, and a front portion 17 and 19, having a cylindrical periphery 21 and 23, respectively, which is externally threaded with cutting edges. The aperture 11 of the nut section 9 has a cylindrical periphery which is internally threaded for receiving and engaging the threads on the front portion 17 of the bolt section 7. The bolt section 7 also comprises a middle portion 25 having a cylindrical periphery 27 which is externally threaded with cutting edges; equal diameters are used for the middle and front portions 25 and 19, respectively. The middle portion 25 is connected to a smooth shaft portion 28. Each of the bolt and nut sections 7 and 9, respectively, have a rear portion or ends 29 and 31, respectively, for attaching the ends of said nuts and bolts 7 and 9, respectively, to said rods 3, as is best shown in FIG. 3. These ends or attachments 29 and 31 are shown as closed and open attachments, respectively, in FIG. 4A, whereas one of said beam means is shown having closed attachments at both ends; after the attachments are installed a staple or a plate (not shown) can be disposed beneath the attachments.

Another preferred embodiment of the beam means 5 is shown in FIG. 4B and is utilized when the system is used for fixing smaller vertebrae. Its middle portion 33 comprises a smooth shaft portion, the diameter of which is slightly less than the diameter of the threaded portion 21 of the front portion 17. Its attachments 29 and 31 are of the closed type.

Figure 1:
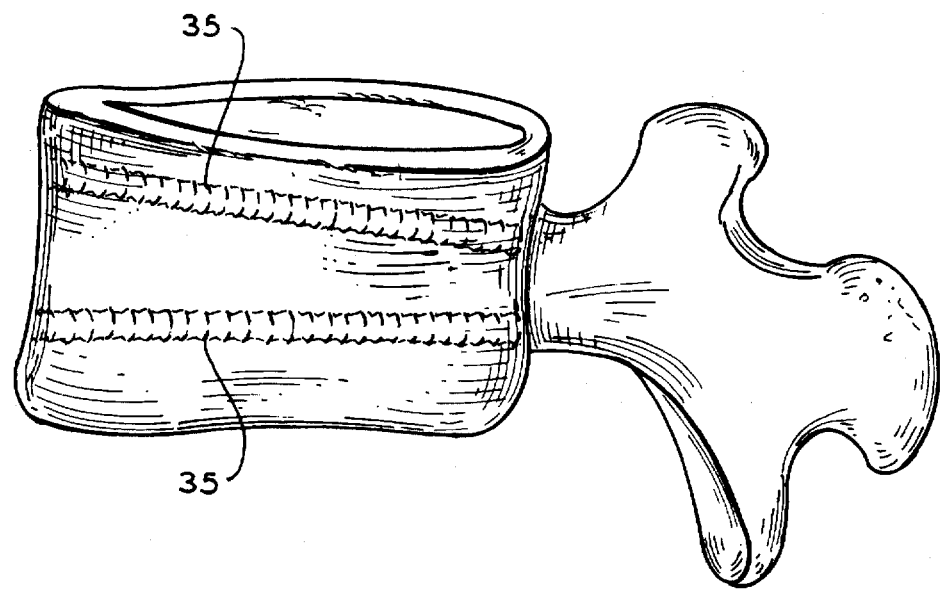
FIG. 1 is a perspective view of an individual vertebra wherein only the threaded apertures which are formed by insertion of a pair of nut and bolt portions of the present invention.

The surgical technique used for implanting the preferred system of the present invention is generally described as follows (for fixing two levels of vertebrae). A portion of the spine and therefore a vertebra is surgically exposed anteriorly and posteriorly simultaneously. Then a one or pair of beam means 5 are inserted through an individual vertebra; more specifically one or two pedicle bolt sections 7 each shown as having a cannulation 11, are inserted from posterior to anterior through the vertebra so as to join its opposite bolt section 7, that is the cannulation 11 of each nut section engages the threads on the front portion 17 of each bolt section 7. The route in the vertebrae or sacrum (FIG. 1) can be prepared over a guide wire utilizing a cannulated tapper, which allows usage of an uncannulated bolt section, if required. The above described procedure is then repeated for the next vertebra level and then three column means or rigid elongated rods 3 are disposed over the anterior and posterior aspects of the two vertebrae and connected to these rods 3. More specifically the rear portions or ends 29 and 31, respectively of the bolt and nut sections 7 and 9, are attached to the rods 3. Such an implanted spinal stabilization system is shown in FIG. 3. Further aspects of the present invention are as follows: the cannulated pedicle bolt accommodates a Kirschner wire ("k-wire") which is used as a pilot locator bolt 7 is posteriorly inserted over a properly placed k-wire (not shown) through its central aperture and through the pedicle portion of the vertebra to form a posterior portion of a threaded aperture 35; the nut 9 is similarly inserted over the k-wire anteriorly through its central aperture to form an anterior portion of the threaded aperture 35—this aperture 35 is seen best in FIG. 2.

Figure 5:
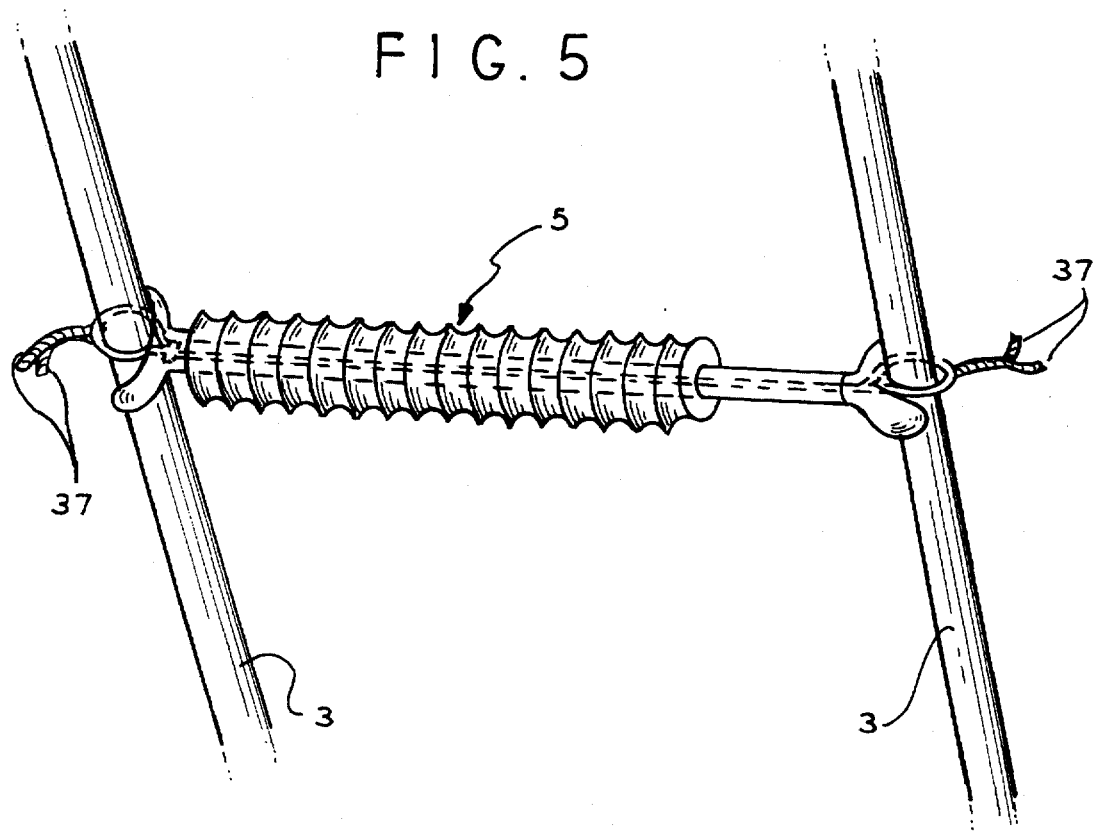
FIG. 5 is a perspective view of a single assembled bolt and nut portions attached at its ends to rods by tie wires.
Figure 2:
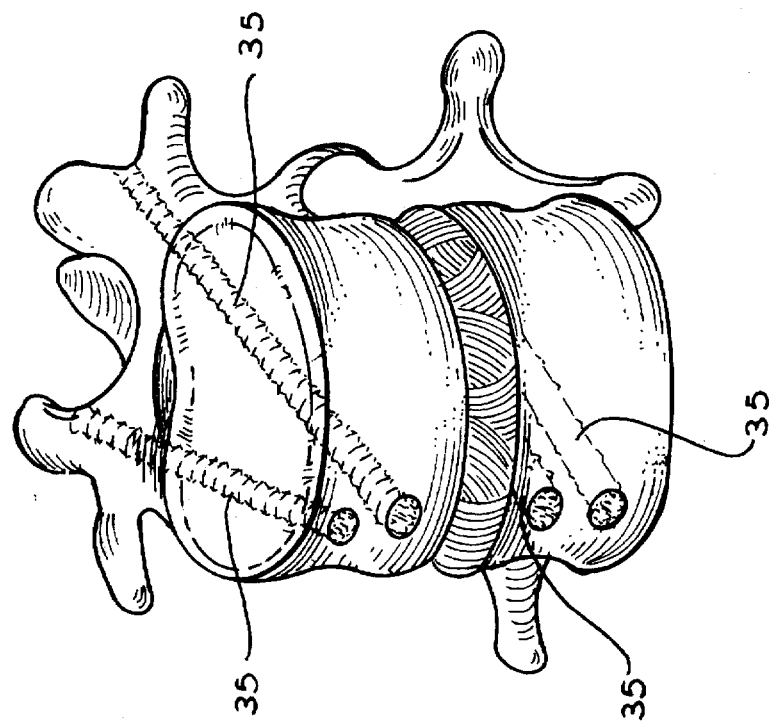
FIG. 2 is a perspective view of two vertebrae and a intervertebral disc wherein only the threaded apertures which are formed by insertion of two pairs of nut and bolt portions of the present invention.

As seen in FIG. 2 and FIG. 3 the two beam means 5 in an individual vertebra are disposed therein in different planes and form a triangle in cross section through said beam means. Also as seen best in FIG. 1 the individual beam means 5 extends through the superior and inferior portions of the same vertebra. The k-wire guide inside the beams means 5 can be replaced with two tie wires 37 which are then twist locked on the rods 3, as seen in FIG. 5, after the beam sections 5 are in place in the vertebrae (not shown in said figure). These twist lock attachments serve to lock the bolt and nut sections 7 and 9, respectively, to the rods 3 to prevent back-off. The nut section 9 has a self-tapping bone screw on its exterior aspects as does the bolt section 7. The bolt section 7 of FIG. 4A preferably has a cutting edge portion 13 around the cannulated opening 11 of 2 mm in length, an externally threaded front portion 17 of greater than 10 mm to 30 mm in length, an externally threaded middle portion 25 of 15 mm to 40 mm in length, and a smooth shaft portion 28 of 20 mm to 40 mm in length. The nut section 9 of FIG. 4A preferably has an externally threaded front portion 19 of about 10 mm to 30 mm in length, and the aperture 11 thereof has an internal machine thread to meet the machines thread on the tip 13 and front portion 17 of the bolt section 7. The pitch of the matching male and female threads are the same. The preferred materials for the bolt and nut sections 7 and 9, respectively, would be $T_1$-6AI-4V, or a similar material because of its mechanical strength properties and corrosion resistance; other possible materials could be a high strength biodegradable polymer such as a high molecular weight PLA, or stainless steel could be used.

Although the present invention has been described and illustrated with respect to a preferred embodiment; it is not to be so limited since modifications and changes can be made therein which are within the full intended scope of the invention.

What is claimed is:

1. A spinal stabilization system for fixing vertebrae and sacrum bodies having anterior and posterior aspects, said system comprising:

a plurality of substantially rigid, elongated column means for being disposed over the vertebrae or sacrum bodies, at least one of said column means for being disposed over an anterior aspect of said bodies and at least another of said column means for being disposed over a posterior aspect of said bodies; and a plurality of substantially rigid, elongated beam means, each of said beam means having a length for and extending through said bodies, each of said beam means including an attachment means on each end thereof for attaching each of said ends to said column means.

2. The system as recited in claim 1 wherein said plurality of substantially rigid, elongated beam means extending through the same vertebra are disposed therethrough on different planes and at different angles relative to the same column means.

3. The system as recited in claim 1 wherein said attachment means of said beam means extends through a longitudinal aperture through said beam means, and extends at least from said posterior aspect to said anterior aspect of a vertebra through which said beam means extends.

4. The system as recited in claim 1 wherein said column means is selected from a group consisting of rods or plates and wherein said plurality of column means includes at least a posterior column means and at least an anterior column means and at least one beam means is attached to one posterior column means and to one anterior column means.

5. The system as recited in claim 1, wherein each said beam means comprises separate bolt and nut sections adapted to enter a body of said bodies and adapted to join each other from opposite aspects of said body after at least a portion of said bolt section and said nut section pass through said body, in opposite directions.

6. The system as recited in claim 5, wherein each of said bolt and nut sections has an aperture extending along longitudinal axes thereof.

7. A spinal stabilization system for fixing vertebrae and sacrum bodies having anterior and posterior aspects, said system comprising:

three rod means being disposed over the vertebrae or sacrum bodies, at least one of said rod means being disposed over an anterior aspect of said bodies and at least another of said rod means being disposed over a posterior aspect of said bodies;

a plurality of elongated beam means, each of said beam means having a length for extending through said bodies and each beam mean including attachment means, at each end thereof, for attaching said beam means to a first rod means disposed over said anterior aspect of said bodies and to a second rod means disposed over said posterior aspect of said bodies, at least two of said beam means attached to a rod means disposed over said anterior aspect of said bodies and on different planes extending through a body of said bodies; and each of said beam means comprising separate bolt and nut sections having longitudinal axes and an aperture, said aperture extending along a longitudinal axis of said nut section, said bolt section and said nut section each comprising a cutting end portion and a front portion, said front portion having a cylindrical periphery externally threaded with cutting edges, said aperture of said nut section having a periphery internally threaded for engaging said externally threaded cutting edges of said front portion of said bolt section.

8. A spinal stabilization system for fixing vertebrae and sacrum bodies having anterior and posterior aspects, said system comprising:

a plurality of substantially rigid, elongated column means for being disposed over said vertebrae or sacrum bodies, at least one of said column means being disposed over an anterior aspect of said bodies and at least another of said column means for being disposed over a posterior aspect of said bodies;

a plurality of substantially rigid, elongated beam means having a length for extending through said bodies and for attaching said beam mean to said column means;

each said beam means comprising separate bolt and nut sections having longitudinal axes which join each other when said sections are inserted into and through an individual said body; and each of said bolt and nut sections comprising a cutting end portion and a front portion having externally threaded cylindrical periphery with cutting edges, and an aperture through said nut section having an internally threaded cylindrical periphery for engaging said cutting edges of said externally threaded cylindrical periphery of said front portion.

9. A spinal stabilization system as in claim 8 and in which each beam means of said plurality of beam means includes an attachment means at each end of said beam means for attaching said beam means to said column means.

10. The system as recited in claim 8, wherein said bolt sections comprises a middle portion having an externally threaded periphery with cutting edges.

11. The system as recited in claim 10, wherein the diameter of the cylindrical peripheries of the middle portion of said bolt section and said front portion of said nut section are substantially equal.

12. The system as recited in claim 8, wherein each of said bolt and nut sections comprise a rear portion for attaching said rear portions of said bolt and nut sections to said column means.

13. The system as recited in claim 8, further comprising wire means extending through said aperture of said beam means for attaching said column means to said beam means.

14. A spinal stabilization system for securing adjacent vertebra of a vertebral column of the body in fixed relation relative to each other, said system comprising:

a plurality of rod means, each rod means being disposed essentially longitudinally along said vertebral column, at least a first of said rod means, disposed along at least a part of a first longitudinal side of said vertebral column and a second of said rod means disposed along a second longitudinal side of said vertebral column, said first rod means and said second rod means disposed essentially opposite each other across said vertebral column;

a plurality of beam means, each of said beam means having a length at least equal to a distance between said first longitudinal side and said second longitudinal side, each of said beam means inserted laterally through at least adjacent bodies, respectively, of said vertebral column and extending at least from said first longitudinal side to said second longitudinal side, each of said beam means including a first attachment means and a second attachment means, said first attachment means positioned at a first end of said beam means and said second attachment means positioned at a second end of said beam means; and said first attachment means for attaching each of said beam means to said first rod means and said second attachment means for attaching each of said beam means to said second rod means.

15. A spinal stabilization system as in claim 14 and in which said plurality of rod means further includes a third rod means disposed along a third longitudinal side of said vertebral column and said second attachment means of at least other beam means of said plurality of beam means is coupled to said third rod means for attaching said at least other beam means to said third rod means.

16. A spinal stabilization system as in claim 14 and in which each beam means of said plurality of beam means has a longitudinal axis and said each beam means includes an aperture extending along said length and having an axis common with said longitudinal axis.

17. A spinal stabilization system as in claim 16 and said attachment means includes a wire means, having a second length, and extending through said aperture, for attaching to said rod means for attaching said beam means to said rod means.

* * * * *